United States Patent [19]

Sarnoff

[11] 4,408,610
[45] Oct. 11, 1983

[54] EMERGENCY ELECTRODE

[75] Inventor: Stanley J. Sarnoff, Bethesda, Md.

[73] Assignee: Survival Technology, Inc., Bethesda, Md.

[21] Appl. No.: 272,973

[22] Filed: Jun. 12, 1981

[51] Int. Cl.³ .............................................. A61B 5/04
[52] U.S. Cl. ..................................................... 128/642
[58] Field of Search ............... 128/639, 642, 784, 785; 273/84 ES; 231/2 E

[56] References Cited

U.S. PATENT DOCUMENTS 3,910,260 10/1975 Sarnoff et al. ...................... 128/639
4,254,764 3/1981 Neward ............................... 128/642

FOREIGN PATENT DOCUMENTS 2247458 4/1974 Fed. Rep. of Germany ...... 128/642
7707275 1/1979 Netherlands ......................... 128/642

OTHER PUBLICATIONS

Shiav, "A Wire Multielectrode . . . Recording," Med. & Biol. Eng., Sep. 1974, p. 721-723.
Caldwell et al., "A Percutaneous Wire Electrode . . .," IEEE Trans. on Bio. Med. Eng. vol. 22, No. 5, pp. 429-432, Sep. 1975.

Primary Examiner—Lee S. Cohen
Attorney, Agent, or Firm—Cushman, Darby & Cushman

[57] ABSTRACT

An emergency electrode comprising a housing assembly, a stressed spring mounted within the housing assembly so as to be released in response to a predetermined manual actuation procedure, an electrode hypodermic needle member mounted within the housing assembly in a sterile condition in cooperating relation with the stressed spring for movement outwardly of the housing assembly in response to the release of the stressed spring so as to penetrate into the muscle tissue of a patient, a bendable wire member extending outwardly from the hollow interior adjacent the leading end thereof in a trailing direction for yieldably retaining the leading end portion of said hypodermic needle in penetrating condition within the muscle tissue of a patient. An electric circuit is completed exteriorly through the needle when in said penetrating relation within the muscle tissue of a patient.

7 Claims, 5 Drawing Figures

U.S. Patent  Oct. 11, 1983  4,408,610
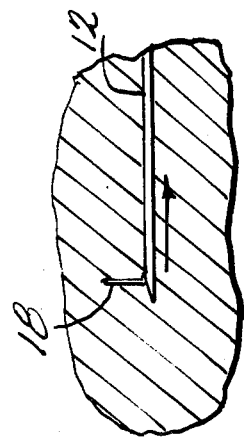
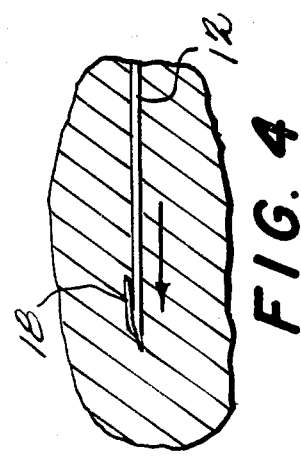
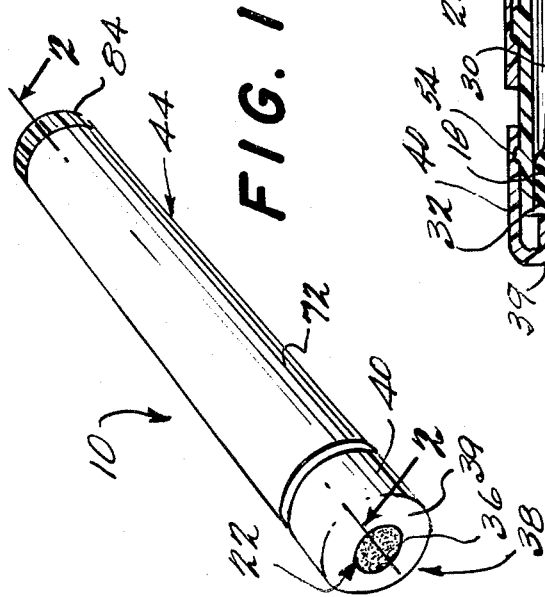
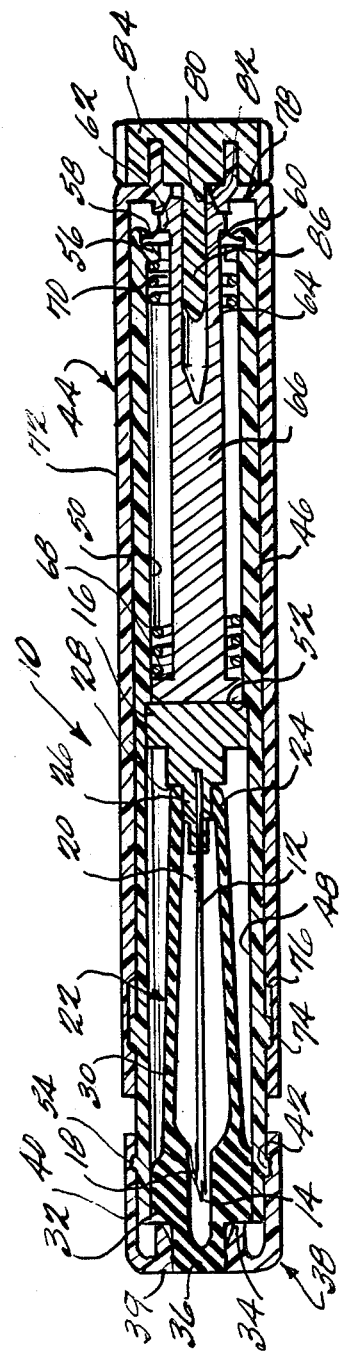
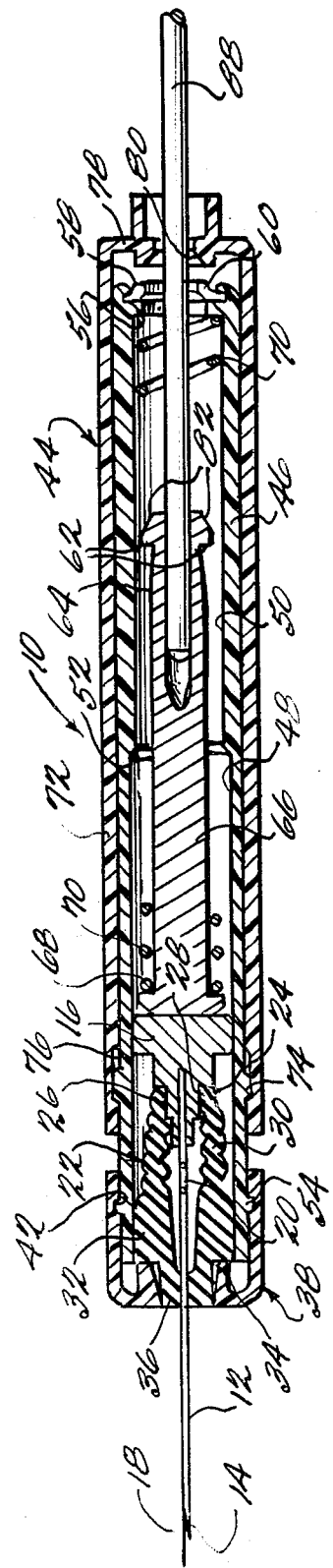

EMERGENCY ELECTRODE

This invention relates to electrodes of the type adapted to be operatively associated with a human being for the purpose of sensing the electrical heart activity of the individual and more particularly to the construction of such electrodes which are particularly useful under emergency conditions, as for example, the emergency conditions such as presented in chemical warfare situations.

It is fundamental in combating chemical warfare to provide each potential chemical warfare patient with an appropriate antidote, preferably in a dosage form contained within an automatic injector. In addition to the basic requirement for administering an antidote there are other treatments which will materially facilitate dealing with personnel disabilities, as for example, a multiple station resuscitator capability as described in commonly assigned application Ser. No. 272,972 filed concurrently herewith. For the purposes of background the specification of the aforesaid application is hereby incorporated by reference into the present specification. For present purposes it is sufficient to note that the multiple station resuscitator unit disclosed in the aforesaid application includes the provision of a life indicator for each of the multiple patients being administered to, which life indicator requires that electrodes be connected with the patient for the purpose of sensing the electrical heart activity of the patient or the ECG signals.

The requirements of an electrode suitable for use under the emergency conditions presented in a chemical warfare situation are indeed more stringent than those presented in typical emergency situations such as encountered by ambulance crews and the like. One of the most difficult requirements presented is the necessity to achieve the electrical connection of the electrode with the patient without exposing skin areas to the chemical agent or nerve gas environment.

It is an object of the present invention to provide an emergency electrode which will meet these severe operating conditions. In accordance with the principles of the present invention this objective is obtained by utilizing a needle, preferably a hypodermic needle as the element of the electrode which is electrically connected with the patient. Preferably, in order to maintain the needle electrical sensing element in a sterile condition prior to use and to assist in effecting the electrical connection thereof with the patient the same is mounted within a housing assembly in a sterile condition in cooperating relation with a stressed spring assembly for movement outwardly of the housing assembly in response to the release of the stressed spring assembly so as to penetrate through any exterior garments or coverings into the muscle tissue of the patient, the arrangement being such that an electrical circuit can be completed exteriorly through the hypodermic needle when disposed within the muscle tissue of the user.

The present invention also includes as an important feature thereof the provision of a bendable wire member extending from the hollow interior of the hypodermic needle outwardly adjacent the leading end thereof in a trailing direction for yieldably retaining the hypodermic needle in penetrated condition within the muscle tissue of the patient with a releasable barb type action.

Another object of the present invention is the provision of an emergency electrode of the type described which is simple in construction, effective in operation and economical to manufacture.

These and other objects of the present invention will become more apparent during the course of the following detailed description and appended claims.

The invention may best be understood with reference to the accompanying drawings, wherein an illustrative embodiment is shown.

In the drawings:

FIG. 1 is a perspective view of an emergency electrode embodying the principles of the present invention showing the same in its stored condition prior to use;

FIG. 2 is an enlarged sectional view taken along the line 2—2 of FIG. 1;

FIG. 3 is a view similar to FIG. 1 illustrating the position of the component parts of the electrode after removal from operative position;

FIG. 4 is an enlarged fragmentary sectional view of the end of the hypodermic needle electrical element showing the barb action of the bendable wire yieldably retaining the same in its operative position; and FIG. 5 is a view similar to FIG. 4 illustrating the manner in which the barb yields during the removal of the hypodermic needle electrical element from the patient.

Referring now more particularly to the drawings, there is shown in FIGS. 1-3 thereof an emergency electrode assembly, generally indicated at 10, which embodies the principles of the present invention. The electrode assembly 10 includes an elongated hypodermic needle 12 of conventional hollow configuration having a leading end pointed, as indicated at 14, for facilitating penetration into the muscle tissue of a patient and a trailing end imbedded in a piston-like support member 16. The hypodermic needle 12 is preferably made of metal, as for example, stainless steel and the support member 16 is likewise made of metal or other suitable electrically conductive material. As shown, the support member 16 is made of brass although it could be made of aluminum or other metals of that type.

Disposed within the hollow interior of the hypodermic needle 12 is a bendable wire member 18. As shown, the bendable wire is extended within the hollow interior of the hypodermic needle 12 to a position adjacent the trailing end thereof engaged within the mounting member 16. In order to retain the bendable wire 18 within the interior of the hypodermic needle the latter is staked or swaged inwardly, as indicated at 20, so as to cause the interior periphery of the hypodermic needle 12 to grip the exterior periphery of the wire member 18. Preferably, the wire member 18 is formed of an electrically conductive material, such as metal, a preferred embodiment shown being copper wire, although stainless steel wire may also be regarded as preferable. In its storage condition, as shown in FIG. 2, the wire member extends outwardly of the leading end 14 of the hypodermic needle 12 and is bent so as to extend in a trailing direction alongside the hypodermic needle. An exemplary diameter of the wire member 18 is 0.009" with an outwardly extending portion of 0.250". It will be understood that these dimensions are merely exemplary and that the actual diameter size can vary therefrom, as well as the extent of the portion of the wire member 18 which extends outwardly of the leading end of the hypodermic needle.

Also as best shown in FIG. 2, the hypodermic needle 12 in its storage position is maintained in a sterile condition by a resilient shroud member, generally indicated at 22. The shroud is made of suitable resilient material as, for example, rubber or the like and includes a trailing end 24 having an opening engaged over a receiving portion 26 of the support member 16 so as to engage rearwardly with a forwardly facing shoulder 28 formed thereon. The shroud includes a relatively thin elongated peripheral wall 30 extending from the apertured end 24 forwardly to a position adjacent the leading end 14 of the hypodermic needle. The latter is enclosed within an enlarged thickened end portion 32 integral with the peripheral wall 30, the thickened end portion providing an outwardly facing annular shoulder 34 and a relatively thin central portion 36 through which the leading end 14 of the needle is adapted to penetrate.

A cap member, generally indicated at 38, of plastic material includes a forward portion 39 which surrounds the shroud end portion 36 and engages the shoulder 34 thereof. The cap member 38 includes a rearwardly extending annular skirt 40 having an annular groove 42 formed on the interior periphery thereof.

The sub-assembly thusfar described including hypodermic needle 12, mounting member 16, bendable wire member 18, shroud 22 and cap member 38 is adapted to be housed within a power pack sub-assembly, generally indicated at 44, which provides a releasable stressed spring for effecting movement of the hypodermic needle outwardly of the shroud and into the muscle tissue of a patient in response to a predetermined manual actuation procedure. As shown, the power pack sub-assembly 44 includes an inner tubular housing member 46 of plastic material providing a forward interior cylindrical chamber 48 of a size to receive the hypodermic needle sub-assembly previously described therein. As shown, the tubular member 46 includes a rearward interior spring chamber 50 of a diameter size less than the diameter size of the chamber 48 so as to provide an annular shoulder 52 which faces in a leading direction so as to engage the rearward outer periphery of the mounting member 16 when the latter is disposed within the chamber 48. In this regard, it will be noted that the enlarged leading end portion 32 of the shroud 22 has an exterior diameter which fits within the open interior diameter of the housing chamber 48. The exterior periphery of the inner tubular housing member 46 has an annular ridge 54 formed therein which is adapted to engage within the annular groove 42 of the cap member 38 when the latter is moved rearwardly over the outer leading extremity of the tubular member 46.

The trailing end of the tubular member 46 includes an apertured end wall 56 and an annular ridge defining an interior annular groove 58 exteriorly adjacent the apertured end wall 56. Mounted within the annular groove 58 is a metallic locking disc 60. The locking disc 60 is centrally apertured and the rearwardly facing surface adjacent the central opening thereof is adapted to engage forwardly facing barbs 62 formed on the rearward ends of spring fingers 64 formed integrally as the rearward portion of a plunger member 66.

Plunger member 66 is preferably made of metal as, for example, brass and the forward end thereof is enlarged so as to define rearwardly facing shoulders 68. A compression helical coil spring 70 is mounted within the chamber 50 in stressed condition with one end engaging shoulders 68 and the other end engaging the inwardly facing annular surface of the apertured end wall 56. The stressed spring 70 tends to resiliently urge the leading surface of the enlarged end of the plunger 68 into abutting engagement with the trailing end surface of the support member 16.

The power pack sub-assembly 44 also includes an outer tubular housing member 72 which is of an interior diameter sufficient to slidably engage over the exterior diameter of the tubular member 46. Housing members 46 and 72 are mounted for limited axial movement with respect to one another by any suitable means such as an annular ridge 74 formed on the exterior periphery of the housing member 46 in rearwardly spaced relation from the ridge 54 and an elongated annular groove 76 formed in the interior periphery of the housing member 72. The tubular member 72 also includes an apertured end wall 78 formed on the rearward end thereof which has an interior annular flange defining a frustoconical barb releasing surface 80. Barbs 62 on the ends of spring fingers 64 are formed with inclined releasing surfaces 82 which face rearwardly and outwardly and are disposed in engagement with the frustoconical surface 80. A safety cap 84 is mounted on the end wall 78 of the housing member 72 and includes a safety pin 86 which engages between the spring fingers 64 so as to prevent the barbs 62 from moving inwardly out of engagement with the locking disc 62.

As previously indicated, the electrode assembly 10 is manufactured by initially assembling the power pack sub-assembly 44 and the remaining components as separate sub-assemblies and then assembling the two sub-assemblies together, as best shown in FIG. 2.

In use, the operator first removes cap 84 so that safety pin 86 no longer prevents the locking barbs 62 from moving inwardly toward one another. The operator then grasps the exterior of the outer housing member 72 and pushes the forward end portion 40 of the cap member 38 into engagement with the portion of the patient where the electrical contact is desired to be established. For example, a desirable location would be in a shoulder muscle, it being understood that two electrode assemblies 10 are required to pick up the ECG signal, with the two being operatively engaged in opposite shoulder muscles. When the operator grasping the outer housing member 72 moves the leading cap member 38 into engagement with the patient's shoulder, the outer housing member 72 is moved axially forwardly with respect to the remaining components causing the interengagement of the frustoconical surface 80 of the outer housing member 72 with inclined barb surfaces 82 to move the barbs toward one another against the flexure provided by the spring fingers 64, thus disengaging barbs 62 from locked engagement with the locking disc 60 and releasing the stressed spring 70 so as to cause the plunger member 66 in engagement with the support member 16 to move the hypodermic needle 12 forwardly with a relatively rapid motion. The leading end 14 of the hypodermic needle penetrates wall 36 of the shroud 22 and moves into the muscle tissue of the patient with the outwardly bent end of the wire member 82 moving inwardly into the muscle tissue with the hypodermic needle in trailing relation as shown in FIG 4. It will be noted that the forward extent of the movement of the hypodermic needle 12 under the action of released stressed spring 70 is determined by the deformation of the shroud wall 30. That is, shroud wall 30 is compressed during the forward movement of the hypodermic needle between the cap member 38 and the support member 16 and progressively retards the forward movement of the hypodermic needle until it is completely halted.

Preferably, in effecting the operative connection as indicated above, the axis of the electrode assembly 10 is disposed in inclined relation to the muscle tissue so that the housing extends at an oblique angle to the surface of the arm after engagement of the needle 12 into the muscle tissue. A suitable alligator clamp or the like may be utilized to attach the electrode to the patient's clothes after engagement and it will be noted that the rearwardly directed end of the bendable wire member 18 serves to yieldably retain the needle 12 within the muscle tissue. Once two assemblies 10 have been engaged in operative position in the manner indicated, the assemblies 10 are then capable of being electrically connected with a device for processing the electrical signals being sensed thereby. In this regard a rodular probe 88 is engaged through the apertured end wall of the outer housing member 72 of each assembly 10 into engagement between the spring fingers 64 thereof so as to complete an electrical connection from the bendable wire member 18, needle member 12, support member 16 and plunger member 66 between the patient and the equipment for processing the electrical signals sensed.

The electrode assembly 10 is removed from the operative position by first removing any mounting restraints connecting the assembly 10 with clothes or the person of the individual to which the apparatus has been operatively connected as, for example, alligator clamps or the like, and then simply grasping the outer housing member 72 and pulling rearwardly. During this action the barbed effect provided by the trailing outwardly extending end portion of the bendable wire member 18 will be overridden and the wire member bent into the position shown in FIG. 5 and then finally moved outwardly in a position of alignment such as shown in FIG. 3. In this way the outwardly extending end portion of the bent wire member 18 serves to yieldably retain the electrode in the form of hypodermic needle 12 within the muscle tissue of the patient so as to pick up the electrical activity of the heart.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. An emergency electrode comprising:
    a housing assembly,
    stressed spring means mounted within said housing assembly so as to be released in response to a predetermined manual actuating procedure,
    an electrode needle structure mounted within said housing assembly in a sterile condition in cooperating relation with said stressed spring means for movement outwardly of said housing assembly in response to the release of said stressed spring means so as to penetrate into the muscle tissue of a patient,
    said needle structure being a hypodermic needle member provided with a hollow interior and having a bendable wire member extending outwardly from said hollow interior adjacent the leading end thereof in a trailing direction for yieldably retaining the leading end portion of said hypodermic needle member in penetrating condition within the muscle tissue of a patient,
    said hypodermic needle member being encased within a resilient shroud within said housing assembly through which the leading end portion thereof extends when moved outwardly of said housing assembly, and
    means for completing an electric circuit exteriorly through said needle structure when in said penetrating relation within the muscle tissue of a patient.

2. An emergency electrode as defined in claim 1 wherein said electric circuit completing means includes a support member of electrically conductive material fixedly connected to the trailing end portion of said needle structure and a plunger of electrically conductive material disposed in electrically conductive operatively fixed relation with respect to said support member, said stressed spring means being connected with said plunger member to move the same in said outward direction in response to the release of said stressed spring means.

3. An emergency electrode as defined in claim 2 wherein said spring means includes a compression coil spring surrounding the major portion of said plunger member and acting between said housing assembly and said plunger member.

4. An emergency electrode as defined in claim 3 wherein said housing assembly includes an inner tubular housing member having a rearward spring chamber within which said plunger member and coil spring are mounted and a communicating forward chamber within which said hypodermic needle member and said support member are mounted.

5. An emergency electrode as defined in claim 4 wherein said plunger member includes spring fingers having releasable locking portions on the rearward free ends thereof, and a locking disc carried by the rearward end of said inner housing member through which said releasable locking portions extend and against which said releasable locking portions are releasably engaged.

6. An emergency electrode as defined in claim 5 wherein said housing assembly includes an outer housing member extending over said inner housing member and mounted for limited axial movement with respect thereto, the rearward end portion of said outer housing member having surface means for moving said releasable locking portions radially inwardly toward one another out of engagement with said locking disc in response to a limited relative axial movement between said housing members in one direction.

7. An emergency electrode as defined in claim 6 including a removable safety pin between said releasable locking portions preventing said movement thereof radially toward one another.

* * * * *